United States Patent [19]

Gerber

[11] Patent Number: 4,675,176

[45] Date of Patent: Jun. 23, 1987

[54] MORAXELLA BOVIS PROTEASE VACCINE

[75] Inventor: Jay D. Gerber, Lincoln, Nebr.

[73] Assignee: Norden Laboratories, Lincoln, Nebr.

[21] Appl. No.: 560,780

[22] Filed: Dec. 12, 1983

[51] Int. Cl.[4] .................... A61K 37/48; A61K 39/00; C12N 9/52
[52] U.S. Cl. ........................................ 424/88; 424/92; 435/220
[58] Field of Search ............................ 424/92, 88, 94; 435/212, 219, 220

[56] References Cited

U.S. PATENT DOCUMENTS

| | | | |
|---|---|---|---|
| 3,197,373 | 7/1965 | Jackson | 424/92 |
| 3,401,219 | 9/1968 | Zeissig | 424/92 |
| 3,853,990 | 12/1974 | Madigan et al. | 424/87 |
| 4,254,098 | 3/1981 | Graham, Jr. et al. | 424/14 |

FOREIGN PATENT DOCUMENTS

107845  10/1982  European Pat. Off. .

OTHER PUBLICATIONS

Frank, Sandra K. and Jay D. Gerber, "Hydrolytic Enzymes of *Moraxella bovis*," *J. of Clin. Imm.*, Feb. 1981, pp. 269-271.

Hughes, D. E., et al., *Am. Journal Vet. Res.*, vol. 38, No. 11 (Nov. 1977) pp. 1905-1907.

Sandhu, T. S. and Franklin H. White, "Extracellular Antigens of *Moraxella bovis*," *Am. Journal of Vet. Res.*, vol. 37, pp. 1119-1122, Sep. 1976.

Windholz, et al., (Ed.) The Merck Index (10th ed.) 1983, p. 1126 (#7721).

Van Bijsterveld, O. P.; "Bacterial Proteases in Moraxella Angular Conjunctivitis," *Amer. J. of Ophthalmology*, vol. 72, No. 1, (1971); pp. 181-184.

Frank et al.; "Hydrolytic Enzymes of *Moraxella bovis*"; *Chemical Abstracts*, vol. 94, No. 15, Apr. 13, 1981; p. 349, Abstract No. 117523e.

Pugh et al., Can. J. Comp. Med. 37:70-78 (1973).

PILIGUARD ™ product bulletin.

*Primary Examiner*—Thomas G. Wiseman
*Assistant Examiner*—Elizabeth C. Weimar
*Attorney, Agent, or Firm*—Edward T. Lentz; Janice E. Williams; Alan D. Lourie

[57] ABSTRACT

Protease produced by *Moraxella bovis* can be used as an immunoprophylactic agent for protection against infection by *M. bovis*.

31 Claims, No Drawings

MORAXELLA BOVIS PROTEASE VACCINE

FIELD OF THE INVENTION

This invention relates to veterinary vaccines and, in particular, to a *Moraxella bovis* bacterin.

BACKGROUND OF THE INVENTION

Moraxella sp. belong to the Family Neisseriaceae. They are strictly aerobic, gram negative, plump rods in pairs or short chains and are oxidase (+) and catalase (+). They are pathogenic in mammals, causing conjunctivitis, sometimes referred to as pink eye.

Bijsterveld, *Amer. J. Ophthamology* 72 (1):181–184 (1971), reports that two species isolated from human clinical infections, *M. liquefaciens* and a new carbohydrate-splitting species, produce different types and amounts of proteases.

*Moraxella bovis* is the etiologic agent of infectious bovine keratoconjunctivitis (IBK), sometimes referred to as bovine pinkeye. Baptista, *Br. Vet. J.* 135:225–242 (1979), reviewed the incidence, symptoms, etiology, treatment and control of IBK.

Frank and Gerber, *J. Clin. Microbiol.* 13(2):269–271(1981), report that *M. bovis* produces tissue damaging enzymes which may initiate or potentiate IBK.

Pugh et al., *Canad. J. Comp. Med.* 37:70–78 (1973), report a role for M. bovis toxins in reactogenicity of live *M. bovis* vaccines.

Henson and Grumbles, *Cornell Vet.* 51:267–284 (1961), report production by *M. bovis* of a hemolytic toxin and a dermonecrotic toxin.

SUMMARY OF THE INVENTION

The invention resides in the discovery that proteolytic enzymes produced by *Moraxella bovis* can be used as an immunoprophylactic agent for prevention of IBK. More particularly, one aspect of the invention is a vaccine capable of inducing immunity to *Moraxella bovis* without serious side effects comprising a vaccinal amount of *M. bovis* protease.

Another aspect of the invention is a vaccine capable of inducing immunity to *M. bovis* without serious side effects comprising a vaccinal amount of a *M. bovis* bacterin which contains a component having proteolytic activity.

DETAILED DESCRIPTION OF THE INVENTION

*Moraxella bovis* strains useful in preparing the vaccine of the invention can be isolated from clinical cases of IBK or can be obtained from available sources. Available sources include, for example, the American Type Culture Collection in Rockville, Md., U.S.A., where *M. bovis* strains are deposited under accession numbers 10900, 17947 and 17948. The bacteria will grow on most common bacterial culture media. However, to prepare the vaccine of the invention, the bacteria is grown in a medium in which the bacteria will produce *M. bovis* protease as the presence of *M. bovis* protease in the vaccine is critical.

Table 1, below, illustrates the criticality of the presence of *M. bovis* protease in the vaccine by showing the relationship of protease activity of various bacterin suspensions to protection of cattle and mice against experimental challenge with virulent *M. bovis*.

Protease activity of a bacterin was measured in Trypticase Soy Agar plates containing 0.5% autoclaved skim milk. Ten microliters of bacterin were added to 3 mm wells. The zones of milk proteolysis were measured after 24 hours by first tracing a 9X projection of the zone and then measuring the zone of proteolysis with a planimeter. The area measured by the planimeter was designated as Units of Protease Activity. Relative protease activity (RPA) is defined as:

$$\frac{\text{Proteolytic units of test bacterin}}{\text{Proteolytic units of reference bacterin}} = RPA$$

The relative potency of a bacterin was determined as follows: Bacterins were diluted 5-fold in 0.15 M NaCl. Mice (16–20 grams) were vaccinated twice, intraperitoneally (IP) at 21-day intervals with 0.5 ml of an appropriate dilution. At least three 5-fold dilutions of bacterin were made with the range selected so the lowest dilution would protect 50% of the vaccinated mice. Mice were challenged IP 7 days following the second vaccination with 0.5 ml dose containing 5–50 $LD_{50}$ of virulent *M. bovis.* All survivors in each test dilution were recorded 3 days following challenge. The 50% protective endpoint dilution ($PD_{50}$) of the bacterin was determined by the method of Reed and Muench, *Amer. J. Hygiene* 27:93–497 (1938). The relative potency (RP) of a bacterin is the ratio of the $PD_{50}$ of that bacterin to the $PD_{50}$ of the reference bacterin. The reference bacterin used herein was *M. bovis* strain Neb-9, grown in culture medium number 4, Table 2, below, for about 9.5 hours at about 33° C., substantially as described below.

TABLE 1

| Vaccination Status | Relative Protease Activity of Bacterin | Relative Potency of Bacterin in Mice | No. of Calves Protected from IBK/No. of Calves Challenged (% protected) | |
|---|---|---|---|---|
| + | 0.40–0.94 | 0.28–1.10 | 22/29 | (70%) |
| + | 0.21 | 0.04 | 1/7 | (14%) |
| – | 0 | 0 | 1/20 | (5%) |

*M. bovis* protease production is greatest when it is grown in enriched media. For example, Table 2 illustrates the effect of growth medium composition on protease production of *M. bovis.* These results, and the results of another experiment shown in Table 3, below, show that protease production is enhanced by addition to the growth medium of a substrate which induces protease production. Examples of such substrates include, but are not limited to, casein or a casein digest; hyaluronic acid, chondroiten sulfate or other tissue constituents contributing to tissue integrity; yeast extract; beef infusion; and tryptone. Other such substrates can be readily identified by testing cells grown in the presence of such substrate for proteolytic activity as described above. Hyaluronic acid and chondroiten sulfate and other factors play a role in binding cells to preserve tissue integrity; the activity of the *M. bovis* protease appears to be directed at such cell binding.

The results show that protease production is especially enhanced by addition of a source of casein, such as a Milk Stock, (or a casein digest such as N-Z Amine A) to the growth medium. For example, compare media 1 and 5, Table 2 and compare media 7 and 8, Table 3.

TABLE 2

| Medium | Units of Protease Activity (Proteolytic Units) | Relative Protease Activity |
|---|---|---|
| 1. RPMI - 1640 .2% Sodium bicarbonate | 0 | 0.00 |
| 2. BME Earle's Powder 10% Fetal Bovine Serum Bovine Corneal Cells | 890 | 0.40 |
| 3. Eugon Broth (360 g) Yeast Extract (60 g) Tween 85 (600 ml) Tween 40 (300 ml) Milk Stock (600 ml) .04% Chondroiten Sulfate (960 ml) .02% Hyaluronic Acid (2,400 ml) Water (7,140 ml) | 1634 | 0.73 |
| 4. Eugon Broth (360 g) Yeast Extract (60 g) Tween 85 (600 ml) .04% Chondroiten Sulfate (960 ml) .02% Hyaluronic Acid (2,400 ml) Milk Stock (600 ml) Water (9800 ml) | 2222 | 1.00 |
| 5. RPMI - 1640 (10 L) .2% Sodium Bicarbonate N-Z Amine A (200 g) | 2536 | 1.14 |

RPMI-1640 is a product of Grand Island Biological Company, Grand Island, N.Y. It contains the following ingredients (mg/L):

| | |
|---|---|
| $Ca(NO_3)_2 \cdot 4H_2O$ (100) | L-methionine (15) |
| KCl (400) | L-phenylalanine (15) |
| $MgSO_4$ (48-84) | L-proline (20) |
| NaCl (6000) | L-serine (30) |
| $Na_2HPO_4$ (800) | L-threonine (20) |
| glucose (2000) | L-tryptophane (5) |
| glutathione (red.) (1) | L-tyrosine (28.94, Na salt) |
| L-arginine (free base) (200) | L-valine (20) |
| L-asparagine (50) | biotin (.20) |
| L-aspartic acid (20) | D-Ca pantothenate (.25) |
| L-cystine (65.15, 2 HCl) | choline Cl (3) |
| L-glutamic acid (20) | folic acid (1) |
| L-glutamine (300) | i-inositol (35) |
| glycine (10) | nicotinamide (1) |
| L-histidine (free base) (15) | p-aminobenzoic acid (1) |
| L-hydroxyproline (20) | pyridoxine HCl (1) |
| L-isoleucine (allo free) (50) | riboflavin (.20) |
| L-leucine (met-free) (50) | thiamine (1) |
| L-lysine HCl (40) | vitamin B12 (.005) |

BME Earle's Powder is a product of the Grand Island Biological Company, Grand Island, N.Y. It contains the following ingredients (mg/L):

| | |
|---|---|
| $CaCl_2$ (200) | L-phenylalanine (16.50) |
| KCl (400) | L-threonine (24) |
| $MgSO_4$ (anhyd.) (97.67) | L-tryptophane (4) |
| NaCl (6800) | L-tyrosine (26) |
| $NaH_2PO_4 \cdot H_2O$ (140) | L-valine (23.50) |
| glucose (1000) | biotin (1) |
| phenol red (10) | D-Ca pantothenate (1) |
| L-arginine HCl (21) | choline chloride (1) |
| L-cystine 2HCl (15.65) | folic acid (1) |
| L-glutamine (292) | i-inositol (2) |
| L-histidine (8) | nicotinamide (1) |
| L-isoleucine (26) | pyridoxal HCl (1) |
| L-lysine HCl (36.47) | riboflavin (.10) |
| L-leucine (26) | thiamine HCl (1) |
| L-methionine (7.5) | |

Eugon Broth is a product of BBL Microbiology Systems, Cockeysville, Md. It contains the following ingredients (mg/L):

| | |
|---|---|
| trypticase peptone (15) | sodium sulfite (.2) |
| phytone peptone (5) | L-cystine (.7) |
| NaCl (4) | dextrose (5.5) |

N-Z Amine A is a pancreatic hydrolysate of casein sold by Sheffield Products, Norwich, N.Y.

Culture medium number 5, Table 2, is herein referred to as the "bacterin medium." It is the preferred medium for production of the bacterin and the protease of the invention.

Results of a similar experiment are reported in Table 3.

TABLE 3

| Medium | Units of Protease activity (Proteolytic Units) |
|---|---|
| 1. Plate Count Broth (4.25 g) 0.5% Yeast Extract (1.25 g) Water (250 ml) | 336 |
| 2. Plate Count Broth (4.25 g) Water (250 ml) | 420 |
| 3. Mueller-Hinton Broth (9.5 g) Water (250 ml) | 423 |
| 4. Mueller-Hinton Broth (9.5 g) 0.5% Yeast Extract (1.25 g) Water (250 ml) | 465 |
| 5. MIE Medium (245 ml) Bacto B (5 ml) | 600 |
| 6. RPMI-1640 (245 ml) Bacto B (5 ml) | 649 |
| 7. Eugon Broth (237.5 ml) 0.5% Yeast Extract (1.25 g) 5% Tween 85 (12.5 ml) | 788 |
| 8. Eugon Broth (225 ml) .05% Yeast Extract (1.25 g) Milk Stock (12.5 ml) 5% Tween 85 (12.5 ml) | 1271 |

Plate Count Broth is a product of Difco Laboratories, Detroit, Mich. It contains 5 g of yeast extract, 10 g of tryptone and 2 g of dextrose per liter of water.

Mueller Hinton Broth is described by Mueller et al., Proc. Soc. Exp. Biol. Med. 48:330 (1941). It contains 300 g of beef infusion, 17.5 g of Acidicase peptone and 1.5 g of starch per liter of water.

MIE medium contains the following ingredients (mg/L).

| | |
|---|---|
| L-cystine (200) | serine (100) |
| tyrosine (200) | uracil (100) |
| leucine (300) | hypoxanthine (20) |
| arginine (340) | inosine (2000) |
| glycine (300) | $K_2HPO_4$ (diab.) (3480) |
| lysine (5) | $KH_2PO_4$ (anhy.) (2720) |
| methionine (100) | yeast extract (10000) |

Bacto Supplement B, a product of Difco Laboratories, Detroit, Mich., is an enrichment for use in supplementing media. It comprises accessory growth factors of fresh yeast. It also contains glutamine coenzyme (v factor), a caboxylase and other growth factors.

Protease production is also dependent on duration of growth. Table 4, which follows, shows relative protease production of a strain of M. bovis cultured for different lengths of time in the bacterin medium.

TABLE 4

| Time (hrs) | Colony Forming Units/ml | Units of Protease activity (Proteolytic Units) |
|---|---|---|
| 0 | $2.4 \times 10^4$ | 0 |
| 3 | $1.3 \times 10^7$ | 650 |
| 4 | $3.0 \times 10^7$ | 788 |
| 5 | $5.0 \times 10^7$ | 800 |
| 6 | $2.3 \times 10^8$ | 1037 |
| 8 | $7.0 \times 10^8$ | 1280 |
| 24 | $1.4 \times 10^9$ | 1660 |

Protease production can also vary depending upon the strain of *M. bovis* employed. For example, under substantially identical conditions of growth, strain NEB-9 produced 2217 proteolytic units, strain FLA-64 produced 1846 proteolytic units and strain ATCC 10900 produced 900 proteolytic units.

A vaccine against *M. bovis* can be prepared from the protease, preferably isolated from the culture medium. More preferably, however, the protease is administered in a bacterin comprising killed *M. bovis* cultured under conditions which promote protease production, such as hereinabove described. Such bacterin preferably contains at least sufficient protease to provoke an immune response, that is, to stimulate production of antibody, to the protease.

Typically, a *M. bovis* seed stock is inoculated into a bacterin medium, as described above. The culture is incubated at 30° to 35° C., preferably 33° C., for 8 to 24 hours with aeration. Following satisfactory growth, the culture is transferred to fresh medium using, for example, a 1 to 5% (vol/vol) inoculum. This second seed passage containing dihydrostreptomycin at a final concentration of 0.01% is cultured at 30° to 35° C., preferably 33° C., for 16 to 30 hours with aeration.

Production cultures are prepared by inoculating a medium with actively growing cells, for example, a 1 to 5% (vol/vol) inoculum of the second seed passage. Such culture is aerated to maintain high oxygen content, preferably at least about 80% dissolved oxygen. The pH is maintained at neutral to slightly alkaline, for example, pH 7.3, by addition of base, for example, 5N NaOH. The culture is incubated at 30° to 35° C., preferably 33° C., for at least 2 hours, preferably 4 to 24 hours, until absorbance at 590 nm is at least 2.0 absorbance units, preferably at least 4.0 absorbance units.

After determining cell density and confirming purity, aeration is discontinued, agitation is slowed and temperature is decreased to below 30° C., preferably to about 25° C. The culture is then inactivated by addition of a known inactivating agent, such as, for example, formaldehyde or gluteraldehyde. The preferred inactivating agent is beta-propiolactone (BPL) at a final concentration of 1:1200 (0.083%) because BPL has been found to be rapidly effective. Inactivation is continued until complete, usually about 2 to 10 hours.

The inactivated culture may be stored at 4° C. until used. A preservative, for example, 10% merthiolate at a final concentration of 1:10,000, is added. The bacterin is adjuvanted with a known adjuvant, for example, Al-(OH)$_3$ or Carbopol (Carbomer, Goodrich) The preferred adjuvant is Quil A at 0.5 mg/ml. Quil A is a saponin. See, Dalsgaard, *Acta Veterin. Scand.* Supp 69:1–40 (1978).

The bacterin is standardized to contain not less than 2.0 absorbance units at 590 nm, and, preferably to contain 4.0 absorbance units at 590 nm, by dilution, if necessary, with, for example, saline. Such dosage unit approximately corresponds to a relative potency (RP), as defined above, of 0.4 or greater.

Alternatively, cells can be removed from the culture medium, before or after inactivation, and the crude supernatant which contains the protease can be employed as the immunoprotective agent. Preferably, however, in this alternative procedure, the protease is purified by standard protein purification techniques, such as by chromatography, and the purified protease is employed as the immuno-protective agent. The protease is adjuvanted and administered in units of relative potency of 0.4 to greater than 1.0, preferably, greater than 1.0.

The vaccine of the invention is administered, preferably, in two 2.0 ml doses subcutaneously in the neck region of calves, three weeks apart. Higher and lower doses, depending, for example, on animal size and relative potency of the vaccine, and other routes and schedules of administration can be used. For example, dose volumes of 1 to 3 ml can be administered intramuscularly or sub-cutaneously around the eyes.

Primary immunization of calves should be initiated at 4 weeks of age and a booster dose given 3 weeks later. Annual revaccination is recommended.

The following Examples of the invention are illustrative and not limiting.

EXAMPLE 1

Master Seed Stock and Challenge Cultures

*M. bovis* was isolated from a calf with IBK. The isolate was passed twice on Trypticase Soy Agar containing 0.5% sheep red blood cells (RBC). The second passage, that is, the Master Seed Stock, identified as strain Neb-9, was grown in the bacterin medium and lyophilized and stored at 4° C. or frozen and stored at −70° C. Strain Neb-9 has been deposited in accordance with the U.S. patent laws and the Budapest Treaty in the American Type Culture Collection, Peoria, Ill., under accession number 39503.

The Master Seed Stock was confirmed to be a pure culture of gram(−) rods having the following characteristics: autoagglutinated; beta-hemolysis; oxidase (+); gelatin (+); caseinase (+); streptomycin resistant; no growth on MacConkey's agar; citrate (−); nitrate (−); and phenylalanine (−).

Standard challenge cultures were prepared by growing strain Neb-9 and a heterologous challenge strain, Neb-1, which had been isolated from another calf with IBK, on Trypticase Soy Agar plates containing 0.5% sheep RBC. Plates were incubated for 24 hours at 33° C. and then for 4 hours at room temperature. The growth was then removed with a sterile cotton swab and suspended in 1 ml of Trypticase Soy Broth. This was frozen at −70° C. as standard challenge seed. One day before calf challenge, the standard challenge culture was thawed. One ml was added to 150 ml of the bacterin medium and grown for 18 hours at 33° C. and then for 5 hours at room temperature. The pathogenicity of the challenge was evaluated by infecting eyes of five-six week old calves with different concentrations of *M. bovis*. The concentration of *M. bovis* was determined by measuring the O.D. at 590 nm. A needleless tuberculin syringe was used to inoculate 0.5 ml of *M. bovis* culture under the third lids of both eyes of each calf. Calves were challenged with either *M. bovis* strain Neb-1 or strain Neb-9. Eyes of calves were examined daily for two weeks for evidence of IBK and then periodically for an additional two weeks.

Extent of disease was measured as follows: A score of 0 indicated that the eye maintaned its normal appearance during the observation period. If the eye was lacrimating at anytime during the observation period it received a score of 1. A score of 2 indicated that the eye was swollen (conjunctivitis) in addition to lacrimating; a score of 3 indicated that keratitis in addition to conjunctivitis (IBK) was evident at any time during the observation period. Results are reported in Table 5, below.

TABLE 5

| *M. bovis* Strain | Absorbance 590 nm | Calf No. | Results of Challenge Left Eye | Results of Challenge Right Eye |
|---|---|---|---|---|
| Neb-1 | 0.15 | 81 | 0 | 0 |
| | 0.34 | 65 | 3 | 0 |
| | 0.68 | 64 | 3 | 3 |
| | 1.5 | 63 | 3 | 3 |
| | 1.5 | 2 | 3 | 3 |
| Neb-9 | 0.34 | 70 | 0 | 3 |
| | 0.68 | 73 | 3 | 0 |

EXAMPLE 2

Bacterin/Protease Vaccine Preparation

A second seed passage of *M. bovis* strain Neb-9 was grown in the bacterin medium for 24 hours at 33° C. to 4.3 absorbance units at 590 nm. Dissolved oxygen was maintained at about 80% or higher by aeration and agitation. The pH was maintained at 7.3 by addition of 5N NaOH. Prior to inactivation with a 1/1200 (0.083%) dilution of beta-propiolactone, the culture was cooled to less than 20° C. with constant agitation and the air and exhaust ports were closed.

Prior to inactivation, the viable count of bacteria in the culture was $4\times10^9$ colony forming units per ml. Inactivation was complete within 2 hours.

Following inactivation, merthiolate solution was added to a final concentration of 1/10,000 and Quil A was added to a final concentration of 0.5 mg/ml. The relative protease activity (RPA) was 0.94.

EXAMPLE 3

Efficacy Test-Bacterin/Protease Vaccine

Four mixed breed calves, 3 to 4 weeks old, were vaccinated with the bacterin described in Example 2. Three mixed breed calves, 3 to 4 weeks old were not vaccinated. The vaccine was administered subcutaneously in the neck region. All vaccinates received 2 doses of the bacterin 21 days apart. Serum was collected for serological testing before vaccination, 21 days following the first vaccination and 7 days following the second vaccination. All calves were challenged with virulent *M. bovis.*

Table 6 shows that all calves vaccinated with the *M. bovis* bacterin developed serum agglutinating antibodies by 28 days following vaccination (7 days following the second vaccination). Eyes of calves were examined daily for two weeks for evidence of IBK and then periodically for an additional two weeks. The bacterin, with a RP of 1.10 and an RPA of 0.94 protected 75 percent (3/4) of the vaccinated calves against IBK. All non-vaccinated calves (3/3) developed IBK.

TABLE 6

Bacterin/Protease Efficacy Test
Serum Agglutination Titers and Results of Challenge

| Vaccinated Status | Calf No. | Reciprocal of Agglutination Titer at Days Post Vaccination 0 | 21 | 28 | Results of Challenge[1] Left Eye | Right Eye |
|---|---|---|---|---|---|---|
| Vaccinated | 32 | 0 | 8 | 32 | 0 | 0 |
| | 42 | 0 | 2 | 64 | 0 | 3 |
| | 45 | 0 | 4 | 16 | 0 | 0 |
| | 46 | 0 | 2 | 16 | 0 | 0 |
| Not Vaccinated | 44 | 0 | 4 | 4 | 0 | 3 |
| | 48 | 0 | 0 | 0 | 3 | 3 |
| | 49 | 8 | 4 | 2 | 0 | 3 |

[1]Scoring:
0 = Eye was normal, no infection.
1 = Eye lacrimating
2 = Conjunctivitis in addition to lacrimation
3 = IBK

EXAMPLE 4

Protease Vaccine Preparation

Supernatant from a second seed passage of *M. bovis* strain Neb-9 grown in RPMI-1640, 2% N-Z Amine A and 0.2% sodium bicarbonate for 21 hours at 33° C. to 7.0 absorbance units at 590 nm was concentrated 70X and fractionated on a 15 mm×940 mm column packed with Bio-Gel p-200 (BioRád). This gave partial separation of a culture component that possessed proteolytic activity and was substantially free of other *M. bovis* antigens. The eluting buffer was 0.02 M Tris, 0.028 M NaCl and 0.02% $NaN_3$, pH 8.0. Fractions containing protease activity were pooled and concentrated. The final concentration factor from 500 ml of culture supernatant was 25X. The relative protease activity was 1.0.

Pooled fractions containing the partially purified protease were combined with Quil A at a final concentration of Quil A of 50 ug/ml.

EXAMPLE 5

Mouse Potency Test-Protease Vaccine

The protease vaccine preparation described in Example 4 and a reference bacterin were diluted 5-fold in 0.15 M NaCl containing 50 ug Quil A per ml. Mice (16-20 grams) were vaccinated twice intraperitoneally at 21 day intervals with 0.5 ml of either a 1/10, 1/50 or 1/250 dilution of the vaccine or the bacterin. Mice were challenged 7 days later with infectious *Moraxella bovis* strain Neb-1 (31.2 $LD_{50}$). All survivors in each test dilution were recorded 3 days following challenge. The $PD_{50}$ of the protease vaccine preparation was 1/43.7. The $PD_{50}$ of the reference bacterin was 1/177.2. These results indicate that protease antigens separate from other antigenic components of *M. bovis* protect mice against *M. bovis* challenge. Protease antigens separate from other antigenic components will also aid in the protection of cattle against *M. bovis* infection. This statement is based on the evidence that there is a direct relationship between the RP, RPA of *M. bovis* bacterins and their effectiveness in protecting cattle against *M. bovis* infection. The bacterin is more effective, however, than protease antigens alone.

While the preferred embodiments of the invention are described above, it is understood that the invention includes all changes and modifications within the scope of the following claims.

I claim:

1. A vaccine capable of inducing immunity to *Moraxella bovis* without serious side effects comprising a vaccinal amount of *Moraxella bovis* protease and an adjuvant to elicit an immunoprotective response in a mammal, wherein each vaccine dose has Relative Protease Activity of 0.4 or greater.

2. The vaccine of claim 1 in which the *Moraxella bovis* protease is isolated from *Moraxella bovis* cells.

3. The vaccine of claim 1, capable of inducing immunity to *Moraxella bovis* in a cow, which comprises a concentrated fraction of supernatant from a culture of *Moraxella bovis* grown in a medium which contains a substrate which induces protease production in addition to other nutrients necessary for cell growth and propagation.

4. The vaccine of claim 3 in which the substrate which induces protease production is a milk stock, casein or a casein digest.

5. The vaccine of claim 4 in which the culture of *Moraxella bovis* is grown at 30° to 35° C. with aeration, at neutral to slightly alkaline pH, until absorbance at 590 nm is at least 2.0 absorbance units.

6. The vaccine of claim 5 in which the culture of *Moraxella bovis* is grown until absorbance at 590 nm is at least 4.0 absorbance units.

7. The vaccine of claim 5 in which the *Moraxella bovis* is strain Neb-9, ATCC 39503.

8. The vaccine of claim 7 in which the medium is RPMI 1640 with 2% of a pancretatic hydrolysate of casein and 0.2% sodium bicarbonate.

9. A vaccine capable of inducing immunity to *Moraxella bovis* in a mammal without serious side effects comprising a vaccinal amount of *Moraxella bovis* bacterin and an adjuvant to elicit an immunoprotective response in the bovine animal, the bacterin containing a component having proteolytic activity in at least an amount sufficient to provoke an immune response in the mammal to the proteolytic component wherein the Relative Protease Activity of each vaccine dose is 0.4 or greater.

10. The vaccine of claim 9, which is capable of inducing immunity to *Moraxella bovis* in a cow, in which the bacterin is an inactivated culture of *Moraxella bovis* grown in a medium which contains a substrate which induces protease production in addition to other nutrients necessary for cell growth and propagation.

11. The vaccine of claim 10 in which the substrate which induces protease production is a milk stock, casein or a casein digest.

12. The vaccine of claim 10 in which the culture of *Moraxella bovis* is grown at 30° to 35° C. with aeration at neutral to slightly alkaline pH, until absorbance at 590 nm is at least 2.0 absorbance units.

13. The vaccine of claim 12 in which the culture of *Moraxella bovis* is grown until absorbance at 590 nm is at least 4.0 absorbance units.

14. The vaccine of claim 12 in which the *Moraxella bovis* is strain Neb-9, ATCC 39503.

15. The vaccine of claim 14 which comprises a culture of *Moraxella bovis* in RPMI 1640 with 2% of a pancreatic hydrolysate of casein and 0.2% sodium bicarbonate, which has been inactivated by addition of beta-propiolactone at a final concentration of 1:1200 and adjuvanted with Quil A to a final concentration of Quil A of 0.5 mg/ml.

16. A method of protecting a mammal against infection by *Moraxella bovis* without serious side effects which comprises administering to the mammal the vaccine of claim 1.

17. The method of claim 16 in which the protease is isolated from *Moraxella bovis* cells.

18. The method of claim 16 in which the protease is administered to a cow as a concentrated fraction of supernatant from a culture of *Moraxella bovis* grown in a medium which contains a substrate which induces protease production in addition to other nutrients necessary for cell growth and propagation.

19. The method of claim 18 in which the substrate which induces protease production is a milk stock, casein or a casein digest.

20. The method of claim 18 in which the culture of *Moraxella bovis* is grown at 30° to 35° C. with aeration, at neutral to slightly alkaline pH, until absorbance at 590 nm is at least 2.0 absorbance units.

21. The method of claim 20 in which the culture of *Moraxella bovis* is grown until absorbance at 590 nm is at least 4.0 absorbance units.

22. The method of claim 20 in which the protease is produced by *Moraxella bovis* strain Neb-9, ATCC 39503.

23. The method of claim 22 in which the medium is RPMI 1640 with 2% of a pancreatic hydrolysate of casein and 0.2% sodium bicarbonate.

24. A method of protecting a mammal against infection by *Moraxella bovis* without serious side effects which comprises administering to the mammal the vaccine of claim 9.

25. The method of claim 24 in which the bacterin is an inactivated culture of *Moraxella bovis* grown in a medium which contains a substrate which induces protease production in addition to other nutrients necessary for cell growth and propagation and in which the vaccine is administered to a cow.

26. The method of claim 25 in which the substrate which induces protease production is a milk stock, casein or a casein digest.

27. The method of claim 24 in which the vaccine is administered in a two dose course subcutaneously in the neck region or around the eyes or intramuscularly in the neck region in a dose volume of 1 to 3 ml.

28. The method of claim 25 in which the culture or *Moraxella bovis* is grown at 30° to 35° C. with aeration, at neutral to slightly alkaline pH, until absorbance at 590 nm is at least 2.0 absorbance units.

29. The method of claim 28 in which the culture of *Moraxella bovis* is grown until absorbance at 590 nm is at least 4.0 absorbance units.

30. The method of claim 28 in which the bacterin is an inactivated culture of *Moraxella bovis* strain Neb-9, ATCC 39503.

31. The method of claim 30 in which a single dose volume of 1 to 3 ml of a culture of *Moraxella bovis* in RPMI 1640 with 2% of a pancreatic hydrolysate of casein and 0.2% sodium bicarbonate, which has been inactivated by addition of beta-propiolacetone at a final concentration of 1:1200 and adjuvanted with Quil A to a final concentration of Quil A of 0.5 mg/ml, is administered subcutaneously in the neck region of a bovine animal.

* * * * *

UNITED STATES PATENT AND TRADEMARK OFFICE
CERTIFICATE OF CORRECTION

PATENT NO. : 4,675,176
DATED : June 23, 1987
INVENTOR(S) : Jay D. Gerber

It is certified that error appears in the above-identified patent and that said Letters Patent is hereby corrected as shown below:

In claim 8, column 9, line 30, "pancretatic" should be "pancreatic".

In claim 28, column 10, line 46, "or" should be "of".

In claim 31, column 10, line 60, "beta-propiolacetone" should be "beta-propiolactone".

Signed and Sealed this

First Day of December, 1987

Attest:

DONALD J. QUIGG

Attesting Officer

Commissioner of Patents and Trademarks